United States Patent
Brown

(10) Patent No.: US 8,059,782 B2
(45) Date of Patent: Nov. 15, 2011

(54) RADIOTHERAPEUTIC APPARATUS

(75) Inventor: Kevin Brown, West Sussex (GB)

(73) Assignee: Elekta AB (publ), Stockholm (SE)

( * ) Notice: Subject to any disclaimer, the term of this patent is extended or adjusted under 35 U.S.C. 154(b) by 0 days.

(21) Appl. No.: 11/886,031

(22) PCT Filed: Mar. 1, 2006

(86) PCT No.: PCT/GB2006/000725
§ 371 (c)(1),
(2), (4) Date: Sep. 10, 2007

(87) PCT Pub. No.: WO2006/095137
PCT Pub. Date: Sep. 14, 2006

(65) Prior Publication Data
US 2008/0165928 A1    Jul. 10, 2008

(30) Foreign Application Priority Data
Mar. 10, 2005   (GB) .................................. 0504897.0

(51) Int. Cl.
*A61N 5/10* (2006.01)
*G21K 1/04* (2006.01)

(52) U.S. Cl. ............................ 378/65; 378/150; 378/153

(58) Field of Classification Search ................ 378/4–20, 378/65, 147, 149–153
See application file for complete search history.

(56) References Cited

U.S. PATENT DOCUMENTS
5,317,616 A    5/1994  Swerdloff et al.
(Continued)

FOREIGN PATENT DOCUMENTS
| EP | 0 314 214 B1 | 5/1989 |
| EP | 1 419 801 A | 5/2004 |
| JP | 7-255718 | 10/1995 |
| WO | WO-97/13552 A | 4/1997 |
| WO | WO-02/069349 A1 | 9/2002 |
| WO | 03/099380 A1 | 12/2003 |

OTHER PUBLICATIONS

Bongartz et al., European Guidelines for MultiSlice CT, Mar. 2004, European Comission, pp. 1-13; www.msct.eu.*

(Continued)

*Primary Examiner* — Anastasia Midkiff
(74) *Attorney, Agent, or Firm* — Nelson Mullins Riley & Scarborough LLP; Anthony A. Laurentano

(57) ABSTRACT

The present invention seeks to provide a radiotherapeutic apparatus that mitigates the various problems found in the techniques such as tomotherapy, IMAT, IMRT and the like. It provides a radiotherapeutic apparatus comprising a source of radiation whose output is collimated by a multi-leaf collimator, and a patient support, the source being rotatable around the support and the support being translatable along the axis of rotation, thereby to move the source helically relative to a patient on the support. The leaves of the MLC are preferably oriented orthogonal to the axis of rotation, to simplify computation of the dose distribution. The apparatus thus moves the patient on the patient support system along the axis of rotation, in the longitudinal direction. Thus, the device has an effectively unlimited treatable volume in the longitudinal direction and avoids the limitations of IMAT and IMRT techniques whilst enabling the use of thin MLC leaves to give a high longitudinal resolution. The apparatus is preferably combined with an optimization system providing a computational service similar to that provided for IMAT and IMRT devices. Essentially the same computational techniques could be used, with appropriate changes to the input conditions and characteristic equations. The long aperture length (compared to tomotherapy) makes the radiation delivery efficient and therefore the delivery of high doses a practicality; hypofractionation and radiosurgery therefore become possible over large treatable volumes.

8 Claims, 1 Drawing Sheet

U.S. PATENT DOCUMENTS

| | | | |
|---|---|---|---|
| 5,724,400 A * | 3/1998 | Swerdloff et al. | 378/65 |
| 5,754,623 A * | 5/1998 | Seki | 378/65 |
| 5,818,902 A | 10/1998 | Yu | |
| 6,052,430 A * | 4/2000 | Siochi et al. | 378/65 |
| 6,335,961 B1 * | 1/2002 | Wofford et al. | 378/65 |
| 6,385,286 B1 | 5/2002 | Fitchard et al. | |
| 6,463,122 B1 * | 10/2002 | Moore | 378/65 |
| 6,618,467 B1 * | 9/2003 | Ruchala et al. | 378/65 |
| 7,015,490 B2 * | 3/2006 | Wang et al. | 250/505.1 |
| 7,295,649 B2 * | 11/2007 | Johnsen | 378/65 |
| 2003/0219098 A1 * | 11/2003 | McNutt et al. | 378/65 |
| 2004/0034269 A1 * | 2/2004 | Ozaki | 600/1 |

OTHER PUBLICATIONS

Japanese Office Action for Application No. 2008-500253, dated Jun. 28, 2011.

Kron, T. et al., "Planning evaluation of radiotherapy for complex lung cancer cases using helical tomotherapy," *Phys. Med. Biol.*, vol. 49(16):3675-3690 (2004).

\* cited by examiner

RADIOTHERAPEUTIC APPARATUS

RELATED APPLICATIONS

This application is a 35 U.S.C. 371 national stage filing of International Application No. PCT/GB2006/000725, filed 1 Mar. 2006, which claims priority to Great Britain Patent Application No. 0504897.0 filed on 10 Mar. 2005 in Great Britain. The contents of the aforementioned applications are hereby incorporated by reference.

FIELD OF THE INVENTION

The present invention relates to a radiotherapeutic apparatus.

BACKGROUND ART

It is known that exposure of human or animal tissue to ionising radiation will kill the cells thus exposed. This finds application in the treatment of pathological cells. In order to treat tumours deep within the body of the patient, the radiation must however penetrate the healthy tissue in order to irradiate and destroy the pathological cells. In conventional radiation therapy, large volumes of healthy tissue can thus be exposed to harmful doses of radiation, resulting in prolonged recovery periods for the patient. It is, therefore, desirable to design a device for treating a patient with ionising radiation and treatment protocols so as to expose the pathological tissue to a dose of radiation that will result in the death of these cells, whilst keeping the exposure of healthy tissue to a minimum.

Several methods have previously been employed to achieve the desired pathological cell-destroying exposure whilst keeping the exposure of healthy cells to a minimum. Many methods work by directing radiation at a tumour from a number of directions, either simultaneously from multiple sources or multiple exposures from a single source. The intensity of radiation emanating from each source is therefore less than would be required to destroy cells, but where the radiation beams from the multiple sources converge, the total intensity of radiation is sufficient to deliver a therapeutic dose.

The treatment may be spread over a number of days or weeks, to allow recovery of the healthy tissue. This should recover more quickly, as it received a lesser dose. Accordingly, repeated doses spaced over time will eventually take a greater toll on the pathological cells.

It is therefore important to deliver the radiation as accurately as possible to the pathological cells whilst minimising the dose to healthy tissue. Progress in this regard allows greater individual doses to be delivered in each treatment step, thereby reducing the total number of treatments required and, in fact, reducing the overall dose delivered to a patient. For example, a prescription of 35 instances of a 2 Gy dose might be replaced by 15 instances of a 3 Gy dose, a technique known as "hypofractionation". Taken to its logical extreme, this might be replaced with a single 45 Gy dose if the dosage delivered to healthy tissue can be reduced significantly. This approach, referred to more typically as radiosurgery, will evidently offer advantages to the patient in that fewer treatments are required and there is no risk of inconsistent positioning between treatments.

Various methods have been proposed to reduce the dose the healthy tissue whilst maximising the dose to pathological tissue. The simplest is to direct the beam of radiation from a number of directions. Thus, at the co-incidence of the beams the dosage with be approximately 'n' times the dosage delivered to other areas, where 'n' is the number of directions employed.

Collimation can also be employed to limit the beam size to the minimum required to illuminate the pathological tissue. Multi-leaf collimators (MLCs) are known, such as that described in EP-A-0,314,214, and these are able to shape the beam to a desired outline.

In WO-A-02/069,349, we proposed a system whereby a beam of radiation was swept across the region of interest whilst its width was modulated. This offers the great advantage of an unlimited length to the treatment area.

In "rotational conformal" collimation, a radiation source is rotated around the patient and collimated with an MLC. The shape of the MLC collimation is varied with the angle of approach so that the width of the beam always conforms to the projected outline of the tumour as seen in the beam direction. This is useful for some shapes but deals poorly with concavities or re-entrant shapes.

IMAT techniques are described in U.S. Pat. No. 5,818,902. This develops the rotational conformal technique further by allowing repeated rotations around the patient. In this way, doses can be built up in the tumour area step-by step. To decide on the MLC shapes and directions, computational methods are used. Each voxel of the region of interest is assigned a "cost function", which reflects the cost associated with a specific dose. Thus, for example, a voxel in the tumour area has a high cost associated with a low dose, whereas a voxel in a healthy area will be opposite. Some sensitive areas such as the spine and the digestive tract can be given cost functions that place a particularly high cost on doses above a certain critical level. Computational processes then seek to minimise the cost function by manipulating the delivery options. IMAT can provide exceptional dose distributions.

IMRT is similar in its computational principles to IMAT, but provides for a series of MLC-shaped beams from the same direction. Thus, the computational load is somewhat reduced.

Tomotherapy is a treatment technique described (for example) in 'Planning Evaluation for complex lung cancer cases using Helical Tomotherapy' T. Kron et al. Phys. Med. Biol. 49 (2004) 3675-3690. In this technique, a modulatable fan beam is produced from a source that is rotated around the patient in a helical fashion. The beam's intensity can be modulated by elements that slide into and out of the path of the fan beam across its width. The dose can be very conformal and the dose distributions achieved are impressive.

SUMMARY OF THE INVENTION

There are distinct problems or limitations with all of the above techniques.

The system of WO-A-02/069,349, for example, only employs a single approach direction. IMAT and IMRT offer excellent dose distributions, as noted, but pressure towards greater resolution requires a higher resolution MLC, which tends to have a smaller aperture. Thus, the treatable volume becomes limited.

Helical tomotherapy offers a delivery efficiency that is exceptionally low. In order to achieve comparable plans, a 25 mm Fan Beam Thickness (FBT) is used, together with a Modulation factor (MF) of at least 3—lower values (higher efficiencies) lead to unacceptable plan quality. This results in 2 Gy dose delivery taking approximately 20 minutes beam on time. The dose rate of the beam source is approximately 10 Gy/min i.e. in 20 minutes the machine is capable of delivering 200 Gy. This means that the efficiency of dose delivery is about 1%. Typically using a conventional MLC, IMRT techniques offer an efficiency of about 500%. This means that to achieve the same leakage dose to the patient, the shielding of a tomotherapy machines needs to be 50 times as good. It also means that the machine consumes about 50 times as much electrical power to deliver each fraction, and generates 50 times as much heat. This may also limit the lifetime of other components.

This also means that hypofractionation techniques are not practicable in the context of helical tomotherapy. A 20 Gy fractional dose would take 200 minutes to deliver i.e. 3½ hours beam on time. Typically, 20 minutes is regarded as the maximum length of time that a patient can lie still. Radiosurgery is less practicable still, as a 50 Gy dose would take 500 minutes, i.e. 8½ hours beam on time.

The present invention seeks to provide a radiotherapeutic apparatus that mitigates the various problems found in the above techniques. It therefore provides a radiotherapeutic apparatus comprising a source of radiation whose output is collimated by a multi-leaf collimator, and a patient support, the source being rotatable around the support and the support being translatable along the axis of rotation, thereby to move the source helically relative to a patient on the support.

It is preferred that the leaves of the MLC are oriented orthogonal to the axis of rotation, as this will considerably simplify computation of the dose distribution. In such a case, it is envisaged that the MLC would not be capable of rotation, distinct from a conventional treatment machine.

The apparatus thus moves the patient on the patient support system along the axis of rotation, in the longitudinal direction. Thus, the device has an effectively unlimited treatable volume in the longitudinal direction and avoids the limitations of IMAT and IMRT techniques. Despite this, thin MLC leaves can still be used to give a high longitudinal resolution.

A limited number of MLC leaves can be used, as the longitudinal motion extends the treatable length. This simplifies the engineering compared to a conventional MLC, where the number of leaves is required to be high enough to cover the treatable area. In this way, the use of thinner MLC leaves for higher resolution no longer implies a smaller treatment field.

The apparatus is preferably combined with an optimisation system providing a computational service similar to that provided for IMAT and IMRT devices. Essentially the same computational techniques could be used, with appropriate changes to the input conditions and characteristic equations.

Such a device offers a large number of treatment variables that can be optimised, thereby enabling similar or better dose distribution quality as compared to IMRT and IMAT. However, the long aperture length (compared to tomotherapy) makes the radiation delivery efficient and therefore the delivery of high doses a practicality; hypofractionation and radiosurgery therefore become possible over the large treatable volume that was previously only available via tomotherapy.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
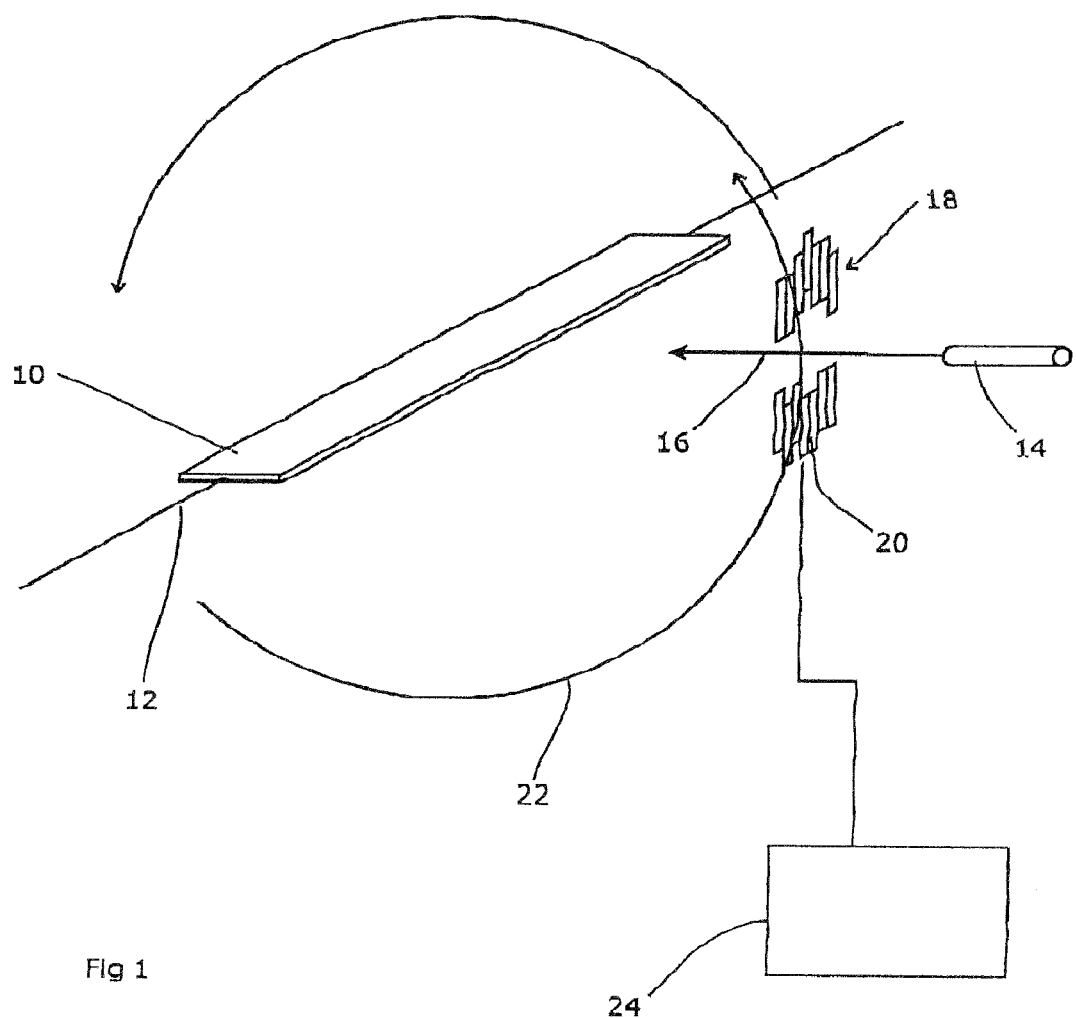
FIG. 1 is a schematic illustration of the geometrical arrangement employed in the present invention.

FIG. 1 shows, in outline, the apparatus used by the present invention. A patient support 10 is provided that is moveable along a longitudinal axis 12. A source of radiation 14 is also provided, on a mount (not shown) that allows it to be rotated around the longitudinal axis 12. Thus, the longitudinal axis of the patient support and the rotational axis of the radiation source are aligned. The source is directed towards the axis 12, such that its beam 16 intersects with the axis.

A multi-leaf collimator (MLC) 18 is provided for the radiation source 14. The leaves 20 of the MLC are oriented perpendicular to the beam 16 and to the axis 12. Accordingly, the leaves are in line with the tangential direction of the source 14 along its rotary path. This therefore collimates the radiation beam from a cone to what can be considered as a plurality of fan beams whose included angle is continuously variable. A computational means 24 is also provided for calculating leaf positions for the multi-leaf collimator 18 as a function of rotation angle of the source 14 to achieve a specified dose distribution.

As the source 14 (and associated collimator 18) is rotated around the axis 12, the patient support 10 is moved along the axis. Thus, relative to a patient on the support 10, the source describes a helix 22.

This idea is probably easiest to understand by considering a special case, in which the patient is moved by the width of one MLC leaf for every rotation of the treatment machine. However, it should be understood that the invention is applicable in other cases. In this special case the radial extent of the treatment field in any transaxial plane is defined by successive leaves in the MLC for successive rotations of the machine. Thereby the dose in a given transaxial slice is built up by the size of the apertures defined by successive leaf pairs. This is analogous to the multiple rotations of the IMAT technique as described in U.S. Pat. No. 5,818,902.

Increasing the FBT of a tomotherapy device in order to reduce the "beam on" time and improve efficiency merely degrades the dose distribution in the sup/inf direction to an unacceptable degree. Decreasing the FBT to improve the dose distribution in the sup/inf direction will increase the beam on time commensurately i.e. 10 mm FBT will result in a beam on time of 50 minutes—an efficiency of dose delivery of about 0.4% or 1 part in 250. According to the present invention, the width of the leaves would ideally be about 3 mm at the isocentre and there should be at least 40 leaves in each opposing bank. A greater or lesser number of leaves could be provided, such as 30, 20, 10 or even at least 3. A total of 40 such leaves would make the length of the collimator 120 mm.

The efficiency is likely to scale by the length of the collimator. Thus, techniques similar to tomotherapy are likely to be 5 times more efficient (120 mm vs. 25 mm). Also, our experience of IMAT techniques shows that the efficiency is typically quite high, of the order of 30%.

The machine could be rotated continuously, but the radiation could be turned off during portions of the arc that do not require radiation. This 30% is of course degraded by the ratio of the tumour length to the collimator length—a 240 mm tumour length would degrade the efficiency to 150%. So these arguments conclude that the efficiency of such a technique is likely to be between 5 and 15%. This is worse than a conventional MLC technique but much better than the tomotherapy technique.

Using leaves of width 3 mm will give a substantially better quality of dose distribution than the FBT of 25 mm of the Tomotherapy technique described. This is because the geometric penumbra of the distributions in the longitudinal direction is likely to be 3 mm and 25 mm respectively for these two techniques.

If the tumour length is less than the length of the collimator the same machine can be used to treat the tumour using a conventional IMAT technique, by leaving the patient support system stationary. The machine can thus be made to deliver both these techniques without modification.

It will of course be understood that many variations may be made to the above-described embodiment without departing from the scope of the present invention.

The invention claimed is:

1. A radiotherapeutic apparatus comprising a source of radiation whose output is collimated by a multi-leaf collimator, and a patient support, the source being rotatable around the support and the support being translatable along the axis of rotation, thereby to move the source helically relative to a patient on the support, wherein the multi-leaf collimator comprises at least three pairs of opposing leaves, each leaf movable such that the radiation output has an included beam angle that is continuously variable to spatially modulate the beam, wherein the multi-leaf collimator is rotationally fixed relative to the source of radiation.

2. A radiotherapeutic apparatus according to claim 1, further comprising computational means for calculating leaf positions for the multi-leaf collimator as a function of rotation angle of the source to achieve a specified dose distribution.

3. A radiotherapeutic apparatus according to claim 1 wherein the multi-leaf collimator has at least 10 leaves.

4. A radiotherapeutic apparatus according to claim 1, wherein the multi-leaf collimator is oriented such that the leaves of the collimator are movable in a direction orthogonal to the axis of rotation.

5. A radiotherapeutic apparatus according to claim 1, wherein the multi-leaf collimator has a length at the isocentre in a direction parallel to the axis of rotation of between 60 mm and 120 mm.

6. A radiotherapeutic apparatus comprising a source of radiation whose output is collimated by a multi-leaf collimator, and a patient support, the source being rotatable around the support and the support being translatable along the axis of rotation, thereby to move the source helically relative to a patient on the support, wherein the multi-leaf collimator is oriented such that the leaves of the collimator are moveable in a direction orthogonal to the axis of rotation to spatially modulate the beam, and wherein a pitch of said helical motion is equal to a width of a leaf of the multi-leaf collimator.

7. A radiotherapeutic apparatus comprising a source of radiation whose output is collimated by a multi-leaf collimator, and a patient support, the source being rotatable around the support and the support being translatable along the axis of rotation, thereby to move the source helically relative to a patient on the support, wherein the multi-leaf collimator comprises at least 3 pairs of opposing leaves, each leaf movable such that the radiation output has an included beam angle that is continuously variable to spatially modulate the beam, and wherein the multi-leaf collimator has a length at an isocentre in a direction parallel to the axis of rotation of between 60 mm and 120 mm.

8. A method of treating a patient using a radiotherapeutic apparatus, the radiotherapeutic apparatus comprising a source of radiation whose output is collimated by a multi-leaf collimator, and a patient support, the source being rotatable around the support and the support being translatable along the axis of rotation, the method comprising:
  simultaneously rotating the source around the support and translating the support along the axis of rotation, thereby moving the source helically relative to a patient on the support; and
  adjusting each of the leaves of the multi-leaf collimator such that the radiation output has an included beam angle that is continuously variable to spatially modulate the beam.

* * * * *